(12) United States Patent
Rosenberg

(10) Patent No.: US 8,932,054 B1
(45) Date of Patent: Jan. 13, 2015

(54) DENTAL OCCLUSION CORRECTING SYSTEM

(71) Applicant: Farel Rosenberg, Bevery Hills, CA (US)

(72) Inventor: Farel Rosenberg, Bevery Hills, CA (US)

(73) Assignee: Farel Rosenberg Living Trust, Beverly Hills, CA (US)

( * ) Notice: Subject to any disclaimer, the term of this patent is extended or adjusted under 35 U.S.C. 154(b) by 0 days.

(21) Appl. No.: 14/084,346

(22) Filed: Nov. 19, 2013

(51) Int. Cl.
- A61C 3/00 (2006.01)
- A61C 7/36 (2006.01)
- A61C 7/18 (2006.01)
- A61C 7/22 (2006.01)

(52) U.S. Cl.
CPC ... *A61C 7/36* (2013.01); *A61C 7/18* (2013.01); *A61C 7/22* (2013.01)
USPC .......................................................... 433/19

(58) Field of Classification Search
USPC ............................................ 433/24, 18–19, 7
See application file for complete search history.

(56) References Cited

U.S. PATENT DOCUMENTS

| | | | |
|---|---|---|---|
| 4,382,783 A | 5/1983 | Rosenberg | |
| 4,472,139 A | 9/1984 | Rosenberg | |
| 5,678,990 A | 10/1997 | Rosenberg | |
| 5,823,772 A | 10/1998 | Vogt | |
| 6,113,390 A | 9/2000 | Sirney | |
| 6,254,384 B1 | 7/2001 | Rosenberg | |
| 7,578,672 B2 * | 8/2009 | Sheikh et al. | 433/19 |
| 8,348,664 B2 * | 1/2013 | Sheikh et al. | 433/19 |
| 2003/0232301 A1 * | 12/2003 | Cleary et al. | 433/19 |
| 2004/0096798 A1 * | 5/2004 | Cleary | 433/18 |
| 2004/0219474 A1 * | 11/2004 | Cleary | 433/19 |

* cited by examiner

*Primary Examiner* — Cris L Rodriguez
*Assistant Examiner* — Hao D Mai
(74) *Attorney, Agent, or Firm* — Albert O. Cota (57) ABSTRACT

A dental occlusion correcting system (DOCS) that is designed to simplify and expedite the correction of Class II dental malocclusions. The DOCS (10) includes a set of upper and lower molar attachment structures (13,14), attached respectively to a person's upper molar and lower molar, a set of upper and lower loosely attached linkages (11,12), and a force module (70). Each of the loosely attached linkages (11,12) includes a link pivitor (50) and a link base (30) which are rotatably connected together through a system of gears and stops and rotational sections (43,44,58,59). The upper and lower loosely attached linkages are connected together, on the same side of a patient's dentition, by a force module. The force module produces upward-backward and downward-forward compression force, commensurate with the force required by a specific dental patient.

15 Claims, 11 Drawing Sheets

DENTAL OCCLUSION CORRECTING SYSTEM

TECHNICAL FIELD

The invention generally pertains to dental correcting systems, and more particularly to a, dental occlusion correcting system that is used to correct Class II malocclusions that are present in both children and adults.

BACKGROUND ART

The dental occlusion correcting system (DOCS) relates to orthopedic and orthodontic appliances for a correcting Class II malocclusion in both children and adults. In a Class II malocclusion a person's lower row of teeth are located behind the upper row of teeth. The malocclusion prevents the normal alignment of the grinding surface of the molars in the upper and lower jaws and thus interferes with normal mastication, as well as presenting a normal visual profile and forward correction of the chin position in a Class II malocclusion.

The present inventive DOCS are an improvement on the dental correcting systems disclosed in the applicant's earlier U.S. Pat. Nos. 4,382,783; 4,472,139; 5,678,990 and 6,254,384. These patents utilize upper and lower links that are threadably adjusted by a screw-based adjustment system. The use of screws for adjustments is undesirable since it creates an undesirable amount of pressure on the first molars to which they are attached. Also, it creates a weakness in a structure which must withstand the considerable pressures generated by the muscles during the opening and especially during the closing of the mouth.

Another disadvantage of the applicant's previously patented systems is the periodic adjustments that are required as the dental treatment progresses. Since the DOCS does not use a screw-based adjustment system, it is possible to use various sizes of DOCS, and to employ an automatically adjustable mechanism for complete treatment.

A search of the prior art did not disclose literature or patents that read directly on the claims of the instant invention. However, the following U.S. patents are considered related.

| PAT. NO. | INVENTOR | ISSUED |
|---|---|---|
| 6,254,384 | Rosenberg | 3 Jul. 2001 |
| 5,678,990 | Rosenberg | 21 Oct. 1997 |

The U.S. Pat. No. 6,254,384 discloses an appliance for orthodontic and orthopedic corrections of Class II and Class III dental malocclusions. The appliance allows a maximum amount of dental movement for the wearer in the horizontal and vertical planes, while exerting forward and backward corrective forces on the upper and lower dental arches and their supporting bone in their closed position, while using a bulky housing to contain angled link bases.

The U.S. Pat. No. 5,678,990 discloses an appliance for correcting Class II malocclusions with automatic adjustments as tooth movement, bone movement, or both occur. The appliance delivers correcting forces by means of a spring which expands through a pre-set, compressed distance. A linkage is employed to increase corrective forces while maintaining a closure.

For background purposes and as indicative of the art to which the invention relates, reference may be made to the following remaining patents found in the search.

| PAT. NO. | INVENTOR | ISSUED |
|---|---|---|
| 6,113,390 | Simey | 5 Sep. 2000 |
| 5,823,772 | Vogt | 20 Oct. 1998 |
| 4,472,139 | Rosenberg | 18 Sep. 1984 |
| 4,382,783 | Rosenberg | 10 May 1983 |

DISCLOSURE OF THE INVENTION

The dental occlusion correcting system (DOCS), which is also referred to as THE BITE GEAR™, is designed to provide a dental practitioner with a safe, easy-to-use and expeditious process for correcting Class II malocclusions.

The DOCS is an external three part inter-arch dental appliance comprising: (a) an upper and lower molar attachment structure, affixed through cementation, to an upper and lower molar, or their equivalent; (b) an upper and lower loosely attached linkage, fixedly attached to the upper and lower molar attachment structures, and consisting of a two piece geared system providing vertical rotation in conjunction with the wearer's mandible; and (c) a spring-like, movement-producing force module, connecting the upper and lower molar attachment structures, on the same side of the dentition.

The use of force modules of increasing lengths, in millimeters, employed unilaterally and bilaterally, advances the mandible and its dentition, transferring upper and backward force to the upper dentition and downward and forward force to the lower dentition, thereby correcting a Class II malocclusion to a normal Class I occlusion.

Orthopedic movement (forward jaw jumping) is further achieved using a scalloped stay plate preventing lower anterior teeth forward slippage that is designed to fit the lingual-inside teeth pattern of an individual patient. The use of the stay plate aids in producing a Class I normal dental occlusion with a normal forward chin position. The stay plate also allows the mouth to be opened and closed during the Class I correction.

In view of the above disclosure, the primary object of the invention is to provide a simple-to-use DOCS that safely expedites the correction of Class II malocclusions.

In addition to the primary object of the invention, it is also an object of the invention to produce a DOCS that:
- replaces external head-gear devices,
- allows for treatment at a younger age than existing devices because it attaches to the upper and lower first molars, which erupt at about age 6, whereas current devices attached to the upper first molar and lower canine, which erupt as about age 10-11,
- can orthopedically jump the bite at onset of treatment,
- advances the mandible and dentition orthodontically through downward and forward forces bilaterally and unilaterally in millimeter increments using a kit of progressively longer force modules, until bite correction is achieved (e.g. Class I),
- can provide accelerated treatment time in bicuspid extraction cases with inter-maxillary molar stabilization or molar distilization, through upper and backward force, provided by the force module,
- decreases the time to treat bicuspid extraction cases, through its forward-downward vector of force assisting the closing forces used in contemporary orthodontics to close lower bicuspid spaces, while preventing forward downward molar movement resulting from the upward backward vector of force on the upper first molars, works in conjunction with inventor's wireless tooth-moving system as described in U.S. Pat. No. 7,234,934 B2, simultaneously correcting and advancing Class II malocclusions with weak retrognathic chins into Class I occlusions with normal profiles.

is dimensioned for patient comfort, does not require a bulky housing and angled linked bases, uses gears to connect the front of the link base to the front of the link pivitor, is easily adjustable to fit various dental patients, controls two dimensions: the vertical (up and down) and the anterior-posterior (front to back) using the force module, while the third dimension, horizontal, is allowed freedom of movement, can include a stay plate that prevents lower dental orthodontic slippage while correcting the mandible-jaw and chin orthopedically into a new forward Class I corrected position, and can use its anterior segment, which rests on immutable bone behind and beneath the roots of the lower anterior teeth, to pit the maxilla (bone) against the mandible (bone), can be used unilaterally or bilaterally as the case requires, employs a snapping means of attaching the force delivering mechanism for ease of use, and is cost effective from both a manufacturer's and consumer's point of view.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms that disclose a preferred embodiment of a dental occlusion correcting system (DOCS) 10. The DOCS 10 is specifically designed to simplify and expedite the correction of Class II malocclusions. The DOCS consists of left and right bite correcting structures, configured to be adjustably attached to the outer surface of either a right dental arch, a left dental arch or to right and left dental arches.

Figure 1:
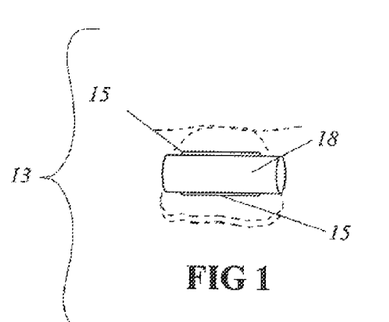
FIG. 1 is a side view of the upper molar attachment structure having an orthodontic band attached preferably by cementation around an upper molar and a corresponding head gear tube preferably welded to the orthodontic band.
Figure 2:
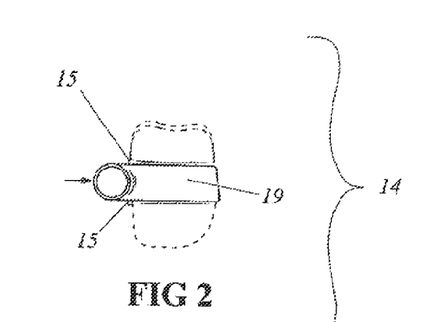
FIG. 2 is a front view of the lower molar attachment structure having an orthodontic band that is attached preferably by cementation around a lower molar with a corresponding lower lip bumper tube preferably welded to the orthodontic band.
Figure 3:
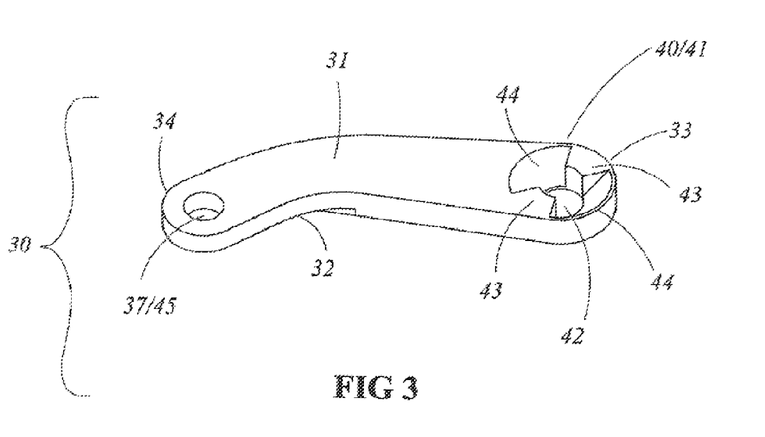
FIG. 3 is an elevational view of the inner surface of an upper and lower, left link base having at the front end a geared female detent, and at the rear end a force module connection consisting of bore.
Figure 4:
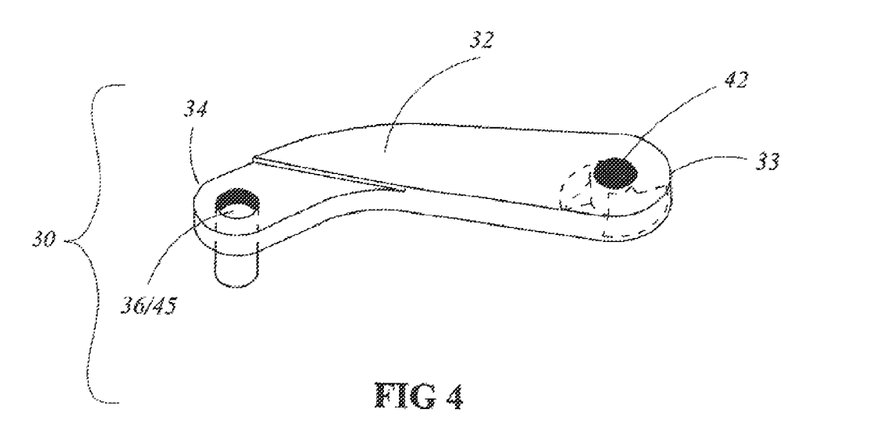
FIG. 4 is an elevational view of the outer surface of an upper and lower, right link base having at the front end a cavity bore, and at the rear end a force module connection consisting of a female detent.
Figure 5:
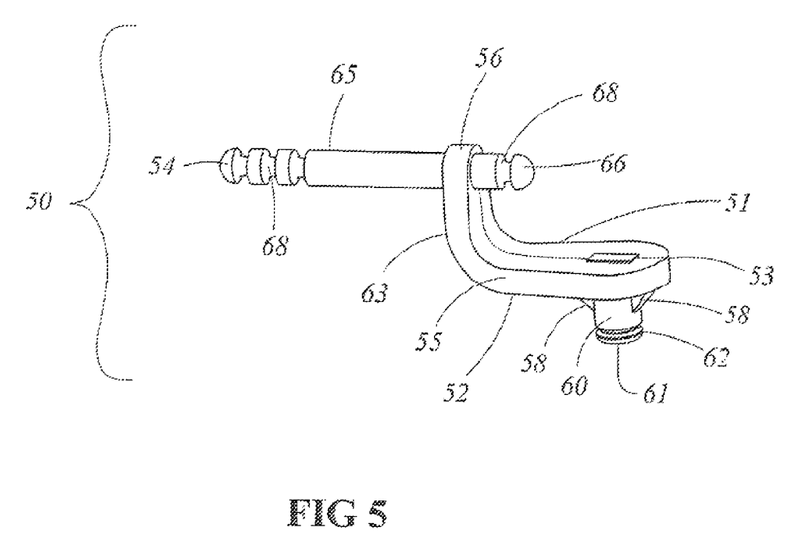
FIG. 5 is a side elevational view of the inner surface of a link pivitor.
Figure 6:
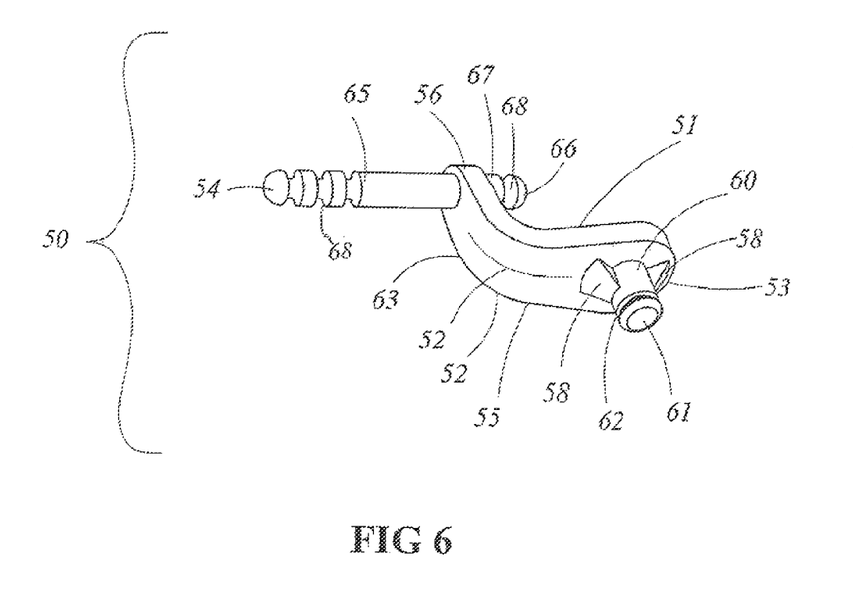
FIG. 6 is a side elevational view of the outer surface of a link pivitor.
Figure 9:
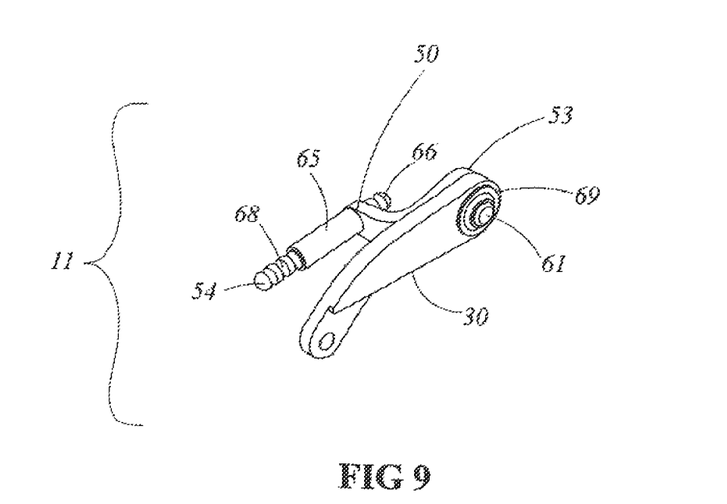
FIG. 9 is a side elevational view of a right, upper loosely attached linkage, consisting of a link pivitor and a right link base connected together by loose attachment means.
Figure 10:
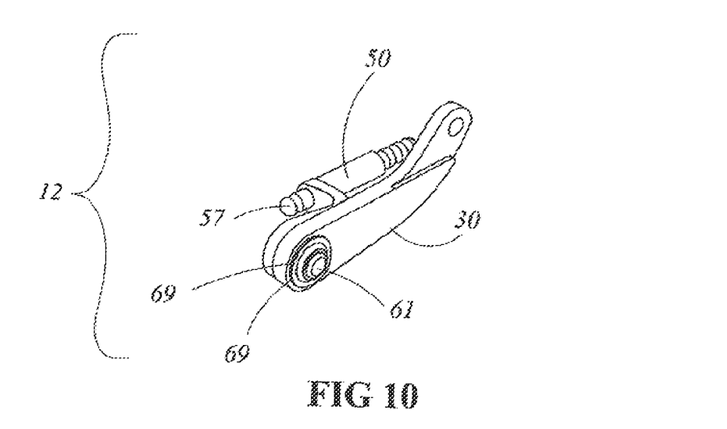
FIG. 10 is a side elevational view of a right, lower loosely attached linkage consisting of a link pivitor and a right link base connected together by loose attachment means.
Figure 11:
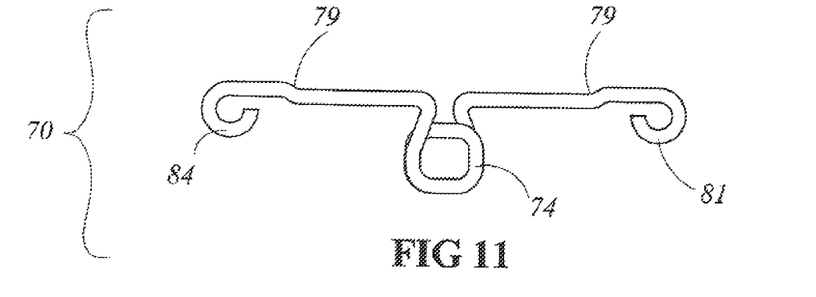
FIG. 11 is a side view of a force module having a central spring section consisting of a helix loop and legs terminating in a force module attachment means comprising a semi attachment loop.
Figure 12:
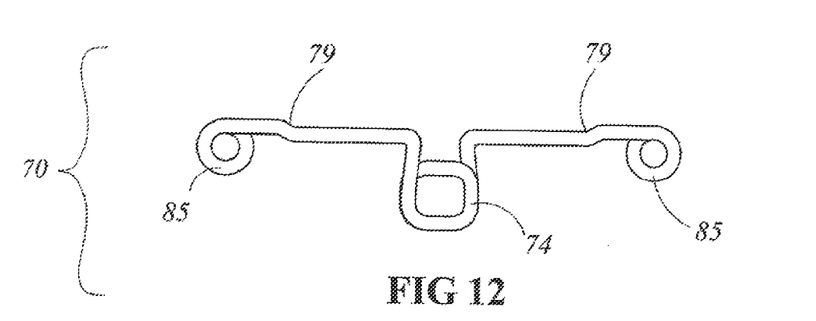
FIG. 12 is a side view of a force module having a central spring section consisting of a helix loop and legs terminating in a force module attachment means comprising a full attachment loop.
Figure 13:
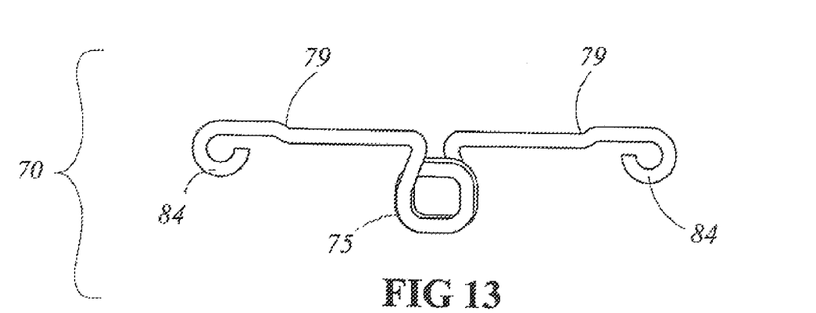
FIG. 13 is a side view of a force module having a central spring section consisting of a multi-helix loop and legs terminating in a force module attachment means comprising a full attachment loop.
Figure 21:
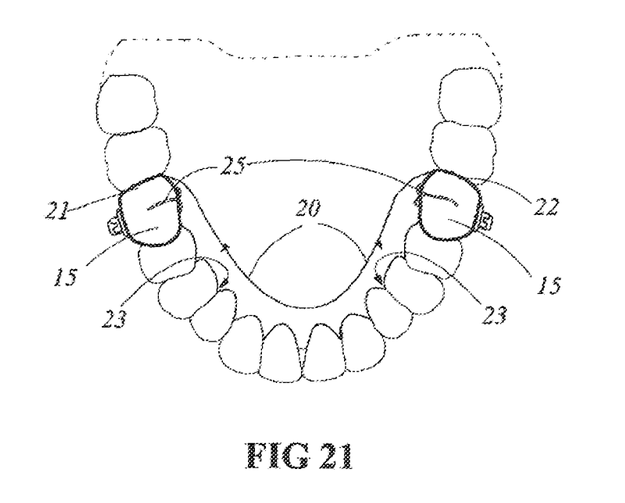
FIG. 21 is a top plan view of a scalloped stay plate terminating at the person's lower first molars on which occlusal rest wires allow proper seating.
Figure 22A:
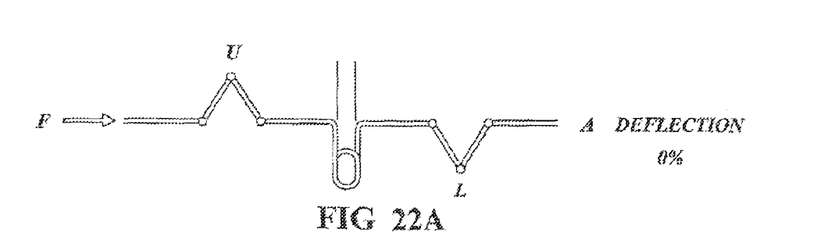
FIG. 22A-D are schematic depictions of the actions of the helix force module as a person's mouth opens and closes.
Figure 22B:
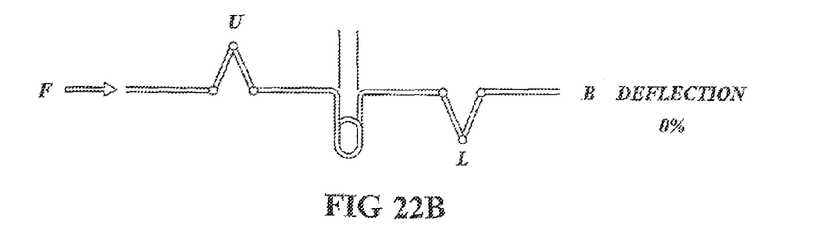
Figure 22C:
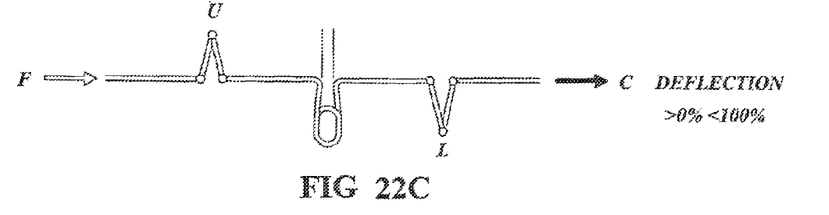
Figure 22D:
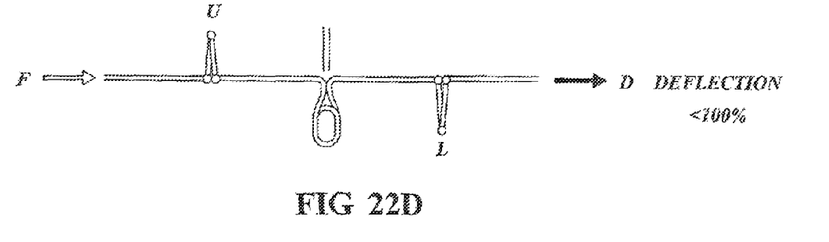

The preferred embodiment of the DOCS 10, as shown in FIGS. 1-2, 4-6, and 14, is comprised of the following major elements: upper and lower molar attachment structures 13, 14, consisting respectively of an upper head gear tube 18, a lower lip bumper tube 19, and an orthodontic band 15, as shown in FIGS. 1 and 2; upper and lower loosely attached linkages 11, 12, as shown in FIGS. 9 and 10, consisting of a link base 30, as shown in FIGS. 3-4, and a link pivitor 50, as shown in FIGS. 5 and 6; a force module 70, as shown in FIGS. 11-15; and a scalloped stay plate 20, as shown in FIG. 21.

For clarity, it should be noted that a selected force module, is used on the left and right sides of a person's dentition. A single link pivitor functions in all four quadrants of the loosely attached linkage: left, right, upper and lower. Two link bases, the mirror images of each other, are utilized; one to function in the upper and lower left positions of the loosely attached linkage, and the other to function in the upper and lower right positions of the loosely attached linkage.

A person's right and left upper and lower molars are comprised of first molars and teeth functioning as first molars, as shown in FIGS. 1-2. The upper and lower molar attachment structures 13, 14 are each comprised of an orthodontic band 15 having an inner surface 16 and an outer surface 17, as shown in FIGS. 1-20. The inner surface 16 is dimensioned to be attached preferably by cementation to the surface of an upper and lower first molar.

The upper molar attachment structure 13 further comprises a head gear tube 18 longitudinally attached preferably by welding to the outer surface 17 of the orthodontic band 15. The lower molar attachment structure 14 further comprises a lip bumper tube 19 longitudinally attached preferably by welding to the outer surface 17 of the orthodontic band 15, as shown in FIGS. 1-2.

The upper and lower molar attachment structures 13, 14, as shown in FIGS. 9-10, are each comprised of a link base 30 and a link pivitor 50. The elements of the link base 30 are an inner surface 31, an outer surface 32, a front end 33, a rear end 34, a male detent 35, a female detent 36, a bore 37, a connecting rod 38, a geared female detent 40, a geared female cavity 41, a cavity bore 42, non-truncated gears and stops 43, truncated rotational sections 44, and a force module connection 45, as shown in FIGS. 3-4.

The geared female cavity 41 is located on the link base's inner surface 31, adjacent the front end 33, and is divided into two truncated rotational sections 44 by two non-truncated gears and stops 43. The cavity 41 terminates in the cavity bore 42 which extends through the link base's outer surface 32, as shown in FIGS. 3-4.

Adjacent the link base's rear end 34 is the force module connection 45 which is selected from the group consisting of a male detent 35, a female detent 36, a bore 37, a screw, a bolt, a nut combination, a rivet, a locking-press fit, a snap, a button, a connecting rod 38, a domed head 39, a diamond head 48, a domed head connecting rod combination, or a diamond head connecting rod combination, as shown in FIGS. 3-4.

The preferred mode of the link base's force module connection 45 is a female detent, as shown in FIG. 4.

Two structurally identical link bases 30, the mirror images of each other, are utilized. A right, upper link base 30 converts into a right, lower link base 30 upon a 180 degree rotation of the link base from front to back, and a left, upper link base 30 converts into a left, lower link base 30 upon a 180 degree rotation of the link base from front to back, as shown in FIGS. 9-10.

A link pivitor 50, as shown in FIGS. 5-6, is used in each upper and lower loosely attached linkage 13, 14, irrespective of left or right position, as shown in FIGS. 9-10.

The elements of the link pivitor 50 are an inner surface 51, an outer surface 52, a first end 53, a second end 54, a trunk section 55, a center shoulder end 56, truncated gears and stops 58 with non-truncated rotational sections 59, an attachment rod, an attachment rod head 61, an indented circumferential zone 62, a center shoulder 63, outer sides 64, a tube insertion rod 65, having a first end 66, a tube bore 67 and circular grooves 68 as shown in FIGS. 5-6.

The trunk section 55 commences as the link pivitor's first end 53 and terminates as the support for the center shoulder 63. The center shoulder 63 is displaced ninety degrees from and on the same plane as the trunk section 55, extending towards the link pivitor's 50 inner surface 51, as shown in FIGS. 5-6.

The tube bore 67 is located in the center shoulder 63, adjacent the center shoulder end 56 through which the tube insertion rod 65 is inserted. The tube insertion rod's first end 66, with at least one circular groove 68, extends in the direction of the link pivitor's first end 53. The tube insertion rod's second end 54, with a plurality of circular grooves 68, also represents the link pivitor's 50 second end 54, as shown in FIGS. 5-6.

The tube insertion rod's second end 54, with its plurality of circular grooves 68, is rotatably and loosely inserted into the upper head gear tube 18 from the front and the lower lip bumper tube from the rear 19. The rod's second end stabilizes and fixes the link pivitor 50, and connects the molar attachment structure and loosely attached linkage, as shown in FIGS. 5-6.

The tube insertion rod 65 in the lower molar attachment structure 14 is further secured by means comprising:

(i) a retaining washer 69 that is dimensioned to be inserted into one of the plurality of circular grooves 68 located on the second end 54, (ii) ligation means located between the tube insertion rod's first and second ends 53,54, or (iii) a bend on the second end 54 of the tube insertion rod 65 that exits the lower lip bumper tube 19.

The link pivitor's attachment rod 60 extends perpendicularly from the outer surface 52 of the trunk section 55, and comprises, at the outer sides 64, angular truncated gears and stops 58 forming non-truncated rotational sections 59, followed by the indented circumferential zone 62 and the attachment rod head 61, as shown in FIG. 6.

Figure 7:
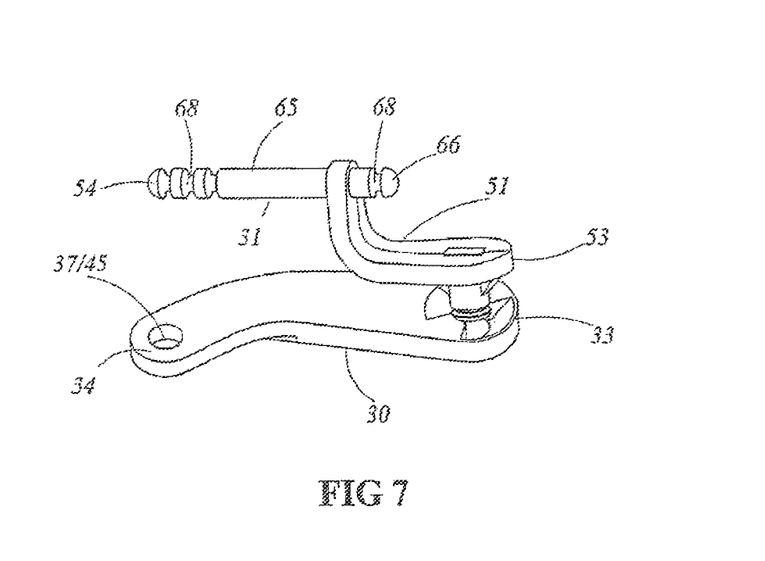
FIG. 7 is an elevational view of the inner surface of a left, upper link base with a link pivitor positioned to be attached to the link base.
Figure 8:
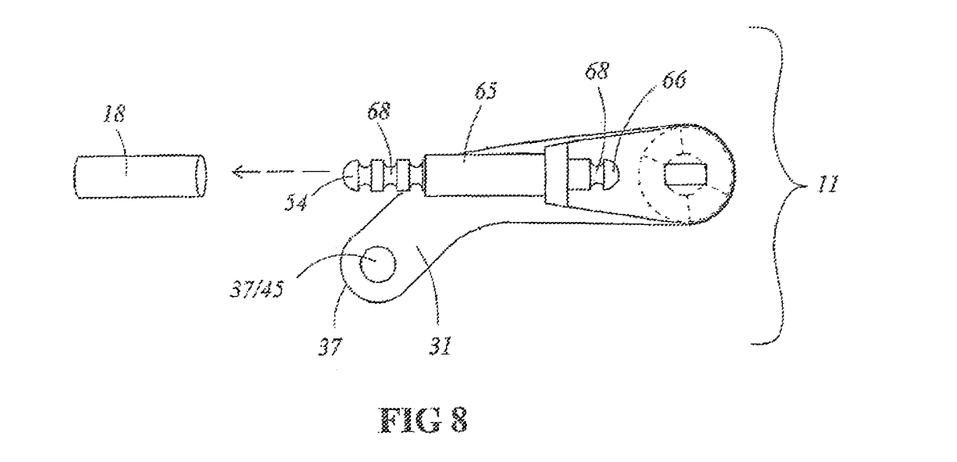
FIG. 8 is a side view of the inner surface of a left, upper link base with a link pivitor attached thereto, and with the link pivitor's tube insertion rod positioned to be inserted into the front of the head gear tube.
Figure 17:
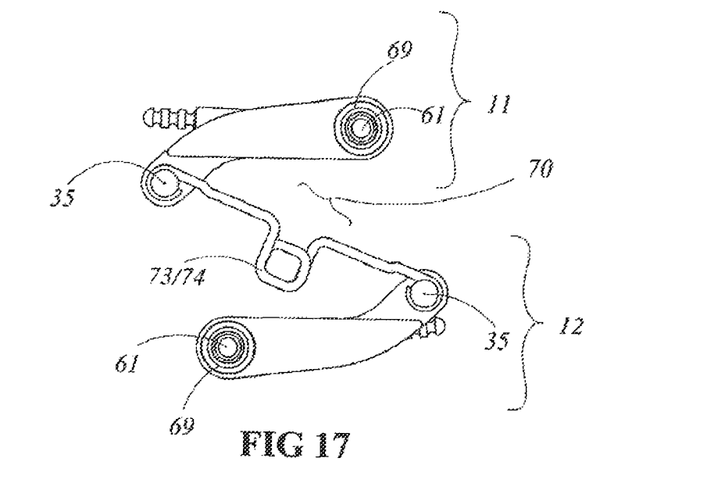
FIG. 17 is an outer side view of right, upper and lower loosely attached linkages connected together by a force module having a central spring section consisting of a helix loop and legs terminating in a force module attachment means consisting of a full attachment loop. The link base in the view has a force module connection consisting of a male detent.

The link pivitor's attachment rod 60, comprising a geared male detent 57, is dimensioned to be inserted into the link base's geared female cavity 41, comprising a geared female detent 40. The rod 60 continues through the link base's cavity bore 42 to the link base's outer surface 32, exposing the link pivitor's indented circumferential zone 62 and attachment rood head 61, which are connected together by attachment means that compress the link pivitor's indented circumferential zone 62 and create one of the loosely attached linkages 13, 14, as shown in FIGS. 7-8. A retaining washer 69, as shown in FIGS. 9 and 10, is located at the link base's outer surface 23, in between the cavity bore and the link pivitor's attachment rod head 61, as shown in FIGS. 9, 10 and 17, in order to ensure loose rotation.

The intersection between the link pivitor's fixed, truncated gears and stops 58 and the link base's non-truncated gears and stops 43 allows for rotation of the link base's truncated rotational sections 44 in the link pivitor's non-truncated rotational sections 59, as shown in FIGS. 7-8. Rotation is stopped by the intersection of the link pivitor's fixed, truncated gears and stops 58 with the link base's non-truncated gears and stops 43, thus preventing disengagement of the DOCS 10. The width of the gears and stops 43, 58 in the link base 30 and link pivitor 50 determines the amount of rotational play within the rotational sections 44, 59, thereby affecting the degree of gear rotation and vertical mouth opening.

Figure 18:
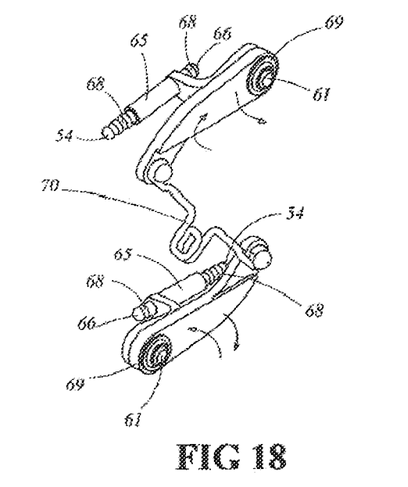
FIG. 18 is an orthographic view of an assembled DOCs showing the movement of counter-clockwise opening and clockwise closing of the link bases.

The opening and closing of a person's mandible alters the position of the link bases 30 within the respective upper and lower loosely attached linkages 11, 12, resulting in vertical counter-clockwise opening and clockwise closing of the link base, as shown in FIG. 18.

The elements that comprise the force module 70 are an upper end 71, a lower end 72, a central spring section 73, a pair of legs 78, and a force module attachment means 81.

The central spring section 73 is selected from the group of springs consisting of a helix loop 74, a multi-helix loop 75, a "U" shape 76, a sinusoid 77 and a leaf spring 78. Extending from the central spring section 73 are the pair of legs 79, as shown in FIGS. 11-15. Each pair terminates in the force module attachment means 81, which is selected from the group consisting of a male detent 82, a female detent 83, a semi attachment loop 84, or a full attachment loop 85 for maximum retention.

The force module's upper end 71 is connected by force module attachment means 81 to the force module connection 45 of the upper loosely attached linkage 11. The force module's lower end 72 is connected by force module attachment means 81 to the force module connection 45 of the lower loosely attached linkage 12.

To avoid interference with the loosely attached linkages 11, 12, the force module's legs 79 are stepped out 80, toward a person's cheeks, as shown in FIGS. 11-14.

The length of the force module 70 controls the advancement of the forward and backward position of a person's maxilla and mandible. Bite correction is achieved through the use of progressively longer force modules 70 which are activated by a person's mandible closing. The mandible can be advanced through downward and forward orthopedic forces exerted by the force module 70. A person's lower first molars are more rapidly advanced through forward orthodontic force exerted upon them, providing accelerated treatment in bicuspid extraction cases. Inter-maxillary molar stabilization or molar distilization is accomplished through upward and backward forces that are exerted by the force module 70.

Figure 19:
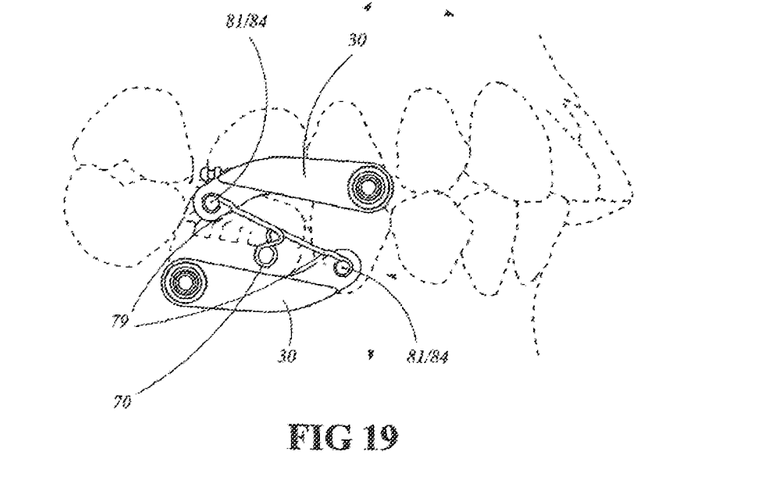
FIG. 19 is a side view of the DOCS attached to a patient's teeth in its active mode, with additional spring power being achieved as the spring force modular's legs pass by each other in different horizontal planes, thus producing maximum modular force and length, correcting a Class II malocclusion to a Class I occlusion.
Figure 20:
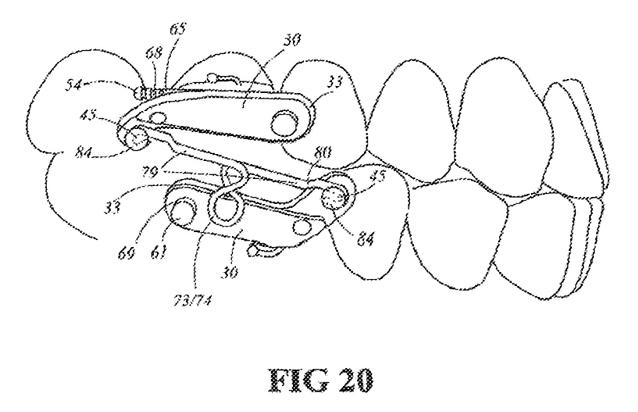
FIG. 20 is a side view of the DOCs attached to a person's teeth having corrected a Class II malocclusion to a Class I occlusion.

The force module 70 produces a compression force as a result of the spring's design, length and width to correct a Class II malocclusion, as shown in FIG. 20, to normal Class I occlusion. Additional spring force is achieved as the module's opposing legs 79 pass by each other in different horizontal planes, thus producing additional modular force and length, as shown in FIGS. 18-20.

The force module attachment means 81 is selected from the group consisting of a male detent 82, a female detent 83, a semi attachment loop 84, a full attachment loop 85, or an attachment bore 86, as shown in FIGS. 11-15.

Figure 14:
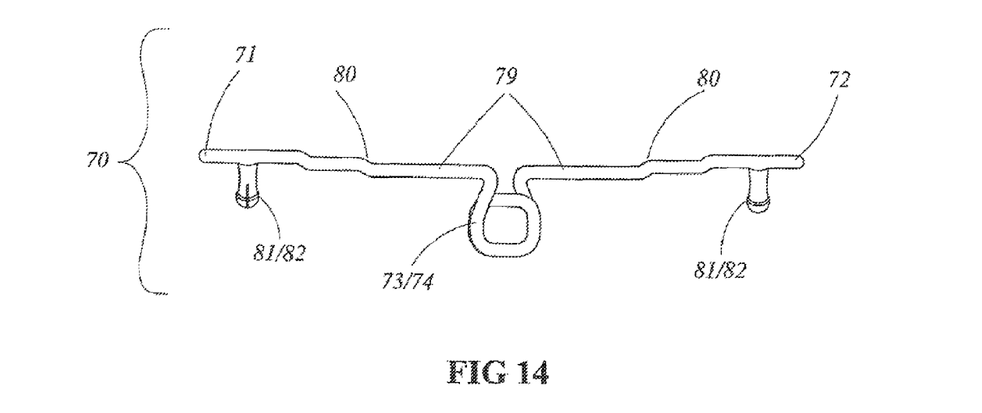
FIG. 14 is a side view of the force module having a central spring section consisting of a helix loop and legs terminating in a force module attachment means comprising a male detent.

The preferred force module attachment means 81 employs a male detent 82, as shown in FIG. 14, that snaps into the link base's force module connection 45 consisting of a female detent 36, as shown in FIG. 4.

Figure 16:
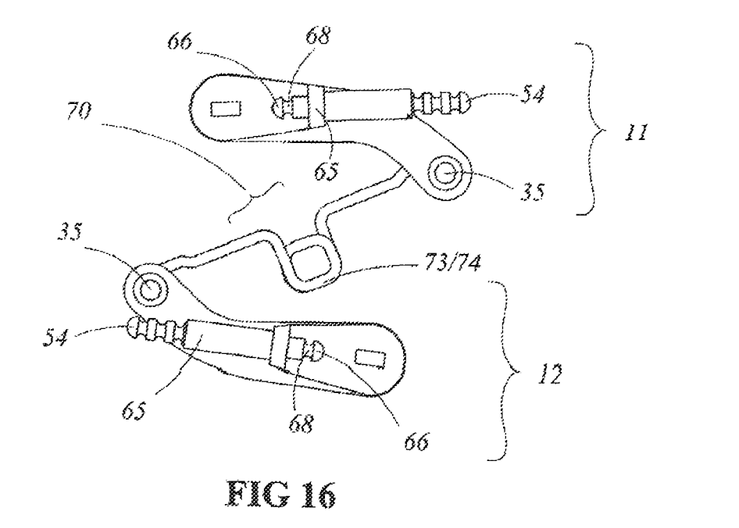
FIG. 16 is an inner side view of right, upper and lower loosely attached linkages connected together by a force module having a central spring section consisting of a helix loop and legs terminating in a force module attachment means comprising a full loop.

The force module attachment means 81 employing a semi-attachment loop 84, a full attachment loop 85, or an attachment bore 86 is connected by attachment means to the link base's force module connection 45 consisting of a male detent 35, preferably with a connecting rod 38 that terminates in a domed head 39, as shown in FIGS. 16, 17 and 20. Rather than making the domed head 39 connecting rod 38 an integral part of the link base 30, the rod 38 may be attached to the link base 30 at the force module connection 45 through press-fitting or other attachment means.

Figure 15:
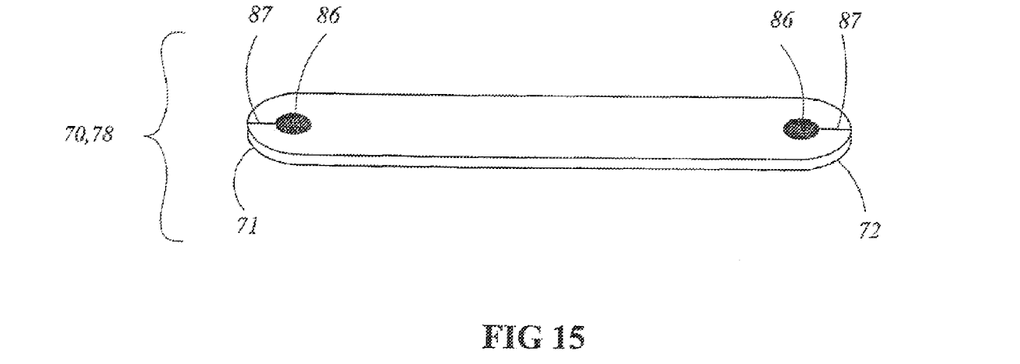
FIG. 15 is a side elevational view of a leaf spring force module with attachment bores and posterior cuts at each end.

The force module 70 consisting of a leaf spring 78 has an upper end 71 and a lower end 72, with attachment bores 86 adjacent to each end. Posterior cuts 87 commence at each end 71,72, and extend into the respective attachment bores 86, as shown in FIG. 15. The posterior cuts 87 are designed to facilitate attachment of the leaf spring 78 attachment bores 86 over the link base's force module connection 45 consisting of a male detent 35, that allows seated rotation of the leaf spring 78 force module 70. While snapping is the preferred means of connecting the leaf spring 78 to the link base's force module connection 45, it may also be connected by direct riveting.

The force module 70 achieves additional compression force as a result of the module's design, length and width. Connection of the force module 70 to the link base's force module connection 45 through snapping means allows for increasing length force modules to be easily used, without the need of replacing the entire upper and lower loosely attached linkages 11,12 for each mandibular advancement, as shown in FIGS. 11-15. Thus, a kit of multiple force modules 70 of increasing length for mandibular advancement simplifies treatment.

The final element that is disclosed is a scalloped stay plate 20, as shown in FIG. 21. The stay plate 20 extends to the rear of the orthodontic bands 15 that are attached to the right and left lower first molars. Located on the rear end of the right orthodontic band 15 is a first terminus 21, and located on the rear end of the left orthodontic band 15 is a second terminus 22. A scalloped section 23, which is specifically designed to fit the dental arch of an individual person, stabilizes the stay plate's position. The stay plate 20 is removable and has a first molar lingual groove rest wire 24 on the left side and on the right is located a rest wire 25, which secures its seating. The stay plate 20 prevents forward slippage of the lower teeth during Class II correction, therefore pitting bone to bone correction to achieve a normal Class I occlusion orthopedically, as shown in FIG. 21.

Schematic depictions of the actions of the DOCS 10 as a person's mouth opens and closes, are shown in FIGS. 22A-D. In each figure there are the letters "F", "U" and "L". The letter "F" indicates a direction, from which a three is exerted on the DOCS. The letter "U" indicates an upper location within a person's mouth relative to the placement of the DOCS. The letter "L" indicates a lower location within a person's mouth relative to the placement of the DOCS.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

The invention claimed is:

1. A dental occlusion correcting system (DOCS) comprising:
   A. an upper molar attachment structure comprising a head gear tube, and a lower molar attachment structure comprising a lip bumper tube; wherein said upper and lower molar attachment structures each has means for being fixedly attached, respectively, to at least one corresponding pair of upper and lower molar orthodontic bands,
   B. an upper attached linkage and a lower attached linkage, each comprising (i) a link base, and (ii) a link pivitor rotatably connected to one another, wherein:
      (i) said link base has a front end and a rear end, wherein said front end comprises a geared female cavity consisting of a geared female detent containing a pair of gears and stops which form truncated rotational sections, wherein said rear end comprises a force module connection selected from the group consisting of a male detent, a female detent, a bore, a screw, a bolt and nut combination, a rivet, a locking-press fit, a snap, a button, a rod, a domed head, and a diamond head;

(ii) said link pivitor has a first end and a second end, wherein said first end comprises a geared male detent consisting of a pair of angular fixed truncated gears and stops which form fixed rotational sections and interface with the geared female detent of the link base; wherein said second end comprises a tube insertion rod;

wherein the tube insertion rod of the link pivitor belonging to the upper attached linkage is rotatable inserted into the head gear tube from a front direction of the head gear tube, and the tube insertion rod of the link pivitor belonging to the lower attached linkage is inserted into the lip bumper tube from a rear direction of the lip bumper tube;

C. a force module comprising a central spring section and a pair of legs extending from the central spring section; the central spring section is selected from the group consisting of a helix loop, a multi-helix loop, a "U" shape, and a sinusoid; each one leg of the pair of legs terminates at a free end formed of an attachment means selected from the group consisting of a semi attachment loop, a full attachment loop, a male detent, a female detent, a snap, and a bore;

wherein the force module connects the upper and lower attached linkages by securing the attachment means of each one leg of the pair of legs to the respective force module connection of the respective link base.

2. The DOCS as specified in claim 1 is made of material that is selected from the group consisting of stainless steel, nitanol, elgiloy, plastic, nylon and a polymer.

3. The DOCS as specified in claim 1, wherein the upper attached linkage and the lower attached linkage are mirror images of each other.

4. The DOCS as specified in claim 1 wherein the central spring section comprises a leaf spring, and the attachment means at the free ends of said each leg of the pair of legs define a bore with a posterior cut, allowing the bore to be pressed over the respective force module connection of the respective link base.

5. The DOCS as specified in claim 1 wherein said link base's force module connection is press-fitted to or integral with said link base.

6. The DOCS as specified in claim 4 wherein said leaf spring is attached to said link base by riveting the attachment means at the free ends of said each leg of the pair of legs onto the respective link base's force module connections.

7. The DOCS as specified in claim 1 wherein a width of the gears and stops in said link pivitor and said link base define an amount of rotational play within the respective rotational sections, affecting a range of a person's vertical mouth opening, wherein rotational angles exceeding 180 degrees produce disengagement of said DOCS.

8. The DOCS as specified in claim 1 wherein an opening and closing of a person's mandible moves said link bases in the respective upper and lower attached linkages, resulting in vertical counter-clockwise opening and clockwise closing of said link bases.

9. The DOCS as specified in claim 1 wherein said link pivitor's truncated gears and stops are secured by insertion of the tube insertion rods into the respective head gear and lip bumper tubes, wherein said link pivitor's gears and stops are enclosed in the truncated rotational sections of said link base, allowing said link base's gears and stops to rotate in said link pivitor's rotational sections, thereby permitting vertical rotation of said link bases as a person's mouth opens and closes.

10. The DOCS as specified in claim 1 wherein inter-maxillary molar stabilization or molar distalization is accomplished as a result of upward and backward forces exerted by said force module.

11. The DOCS as specified in claim 1 wherein the attachment means of the force module consists of a semi-loop or a full loop that is connected by snapping means to said link base's force module connection consisting of a male detent.

12. The DOCS as specified in claim 11 wherein said semi-loop or full lop is flexible and expands over said link base's male detent to securely seat and rotate over the male detent.

13. The DOCS as specified in claim 1 wherein said force module is provided in plurality thereof in a kit, having increasing lengths to advance a person's mandible and dentition; wherein said plurality of force modules can be used unilaterally or bilaterally and without requiring the replacement of said upper and lower attached linkages.

14. The DOCS as specified in claim 1 further comprises a retaining washer that is placed in between said link base and said link pivitor.

15. The DOCS as specified in claim 1 wherein said pair of legs of the force module are stepped out toward a person's cheeks to avoid interference with the attached linkage.

* * * * *